US012661474B2

(12) United States Patent
Baldus et al.

(10) Patent No.: US 12,661,474 B2
(45) Date of Patent: Jun. 23, 2026

(54) RECEPTACLE CONTAINER HAVING MONITORING UNIT

(71) Applicant: Dürr Dental SE, Bietigheim-Bissingen (DE)

(72) Inventors: Fabian Baldus, Vallendar (DE); Jörg Hillen, Nörtershausen (DE); Oleg Batosky, Boppard-Oppenhausen (DE); Jonas Marner, Urbar (DE)

(73) Assignee: Dürr Dental SE, Birtigheim-Bissingen (DE)

( * ) Notice: Subject to any disclaimer, the term of this patent is extended or adjusted under 35 U.S.C. 154(b) by 55 days.

(21) Appl. No.: 18/493,403

(22) Filed: Oct. 24, 2023

(65) Prior Publication Data

US 2024/0131484 A1    Apr. 25, 2024
US 2024/0226830 A9    Jul. 11, 2024

(30) Foreign Application Priority Data

Oct. 25, 2022    (DE) ......................... 102022003990.7

(51) Int. Cl.
*A61M 16/08*    (2006.01)
*F16L 39/00*    (2006.01)
*B01F 35/213*    (2022.01)

(52) U.S. Cl.
CPC ......... *A61M 16/0816* (2013.01); *F16L 39/00* (2013.01); *B01F 35/213* (2022.01)

(58) Field of Classification Search
CPC .............. A61M 16/0816; A61M 16/06; A61M 2202/0283; A61M 16/009; A61M 16/085; F16L 39/00; B01F 35/213

USPC ......... 285/129.1, 130.1, 131.1, 132.1, 124.1, 285/124.4, 124.5
See application file for complete search history.

(56) References Cited

U.S. PATENT DOCUMENTS

| | | | | | |
|---|---|---|---|---|---|
| 861,302 | A | * | 7/1907 | MiBach | E03C 1/284 285/129.1 |
| 4,521,038 | A | * | 6/1985 | Cerny | A61M 16/08 128/911 |
| 4,621,634 | A | * | 11/1986 | Nowacki | A61M 16/08 604/905 |
| 4,938,251 | A | * | 7/1990 | Furrow | F16L 39/02 285/12 |
| 5,101,817 | A | * | 4/1992 | Etter | A61M 16/08 128/207.14 |
| 5,479,920 | A | * | 1/1996 | Piper | A61M 16/0833 128/204.23 |
| 8,939,471 | B2 | * | 1/2015 | Hawboldt | F16L 51/00 285/132.1 |
| 10,882,016 | B2 | | 1/2021 | Baldus | |
| 2012/0136272 | A1 | * | 5/2012 | Varis | A61M 16/0816 600/543 |
| 2015/0083121 | A1 | * | 3/2015 | Fisher | A61M 16/0051 128/205.13 |

(Continued)

FOREIGN PATENT DOCUMENTS

| | | | |
|---|---|---|---|
| DE | 7439876 | U | 4/1975 |
| DE | 102015010684 | A1 | 2/2016 |
| DE | 102020201172 | A1 | 8/2021 |

*Primary Examiner* — David Bochna
(74) *Attorney, Agent, or Firm* — Chiesa Shahinian & Giantomasi PC

(57)    ABSTRACT

A receptacle container for supplying a fluid into a body or body component having a connected monitoring unit in order to monitor a fluid reaction.

18 Claims, 2 Drawing Sheets

(56) References Cited

U.S. PATENT DOCUMENTS

| | | | | |
|---|---|---|---|---|
| 2016/0325070 A1* | 11/2016 | Lu | ..................... | A61M 16/0808 |
| 2017/0259018 A1* | 9/2017 | Blasdell | .............. | A61M 16/009 |
| 2020/0001035 A1* | 1/2020 | VanPelt | ............ | A61M 16/0051 |
| 2021/0003236 A1* | 1/2021 | Echtle | ................. | F16L 33/2073 |
| 2021/0008321 A1* | 1/2021 | Schiappa | .......... | A61M 16/0683 |
| 2023/0075356 A1 | 3/2023 | Schaich | | |
| 2023/0405259 A1* | 12/2023 | Ishikita | ................. | B33Y 80/00 |

* cited by examiner

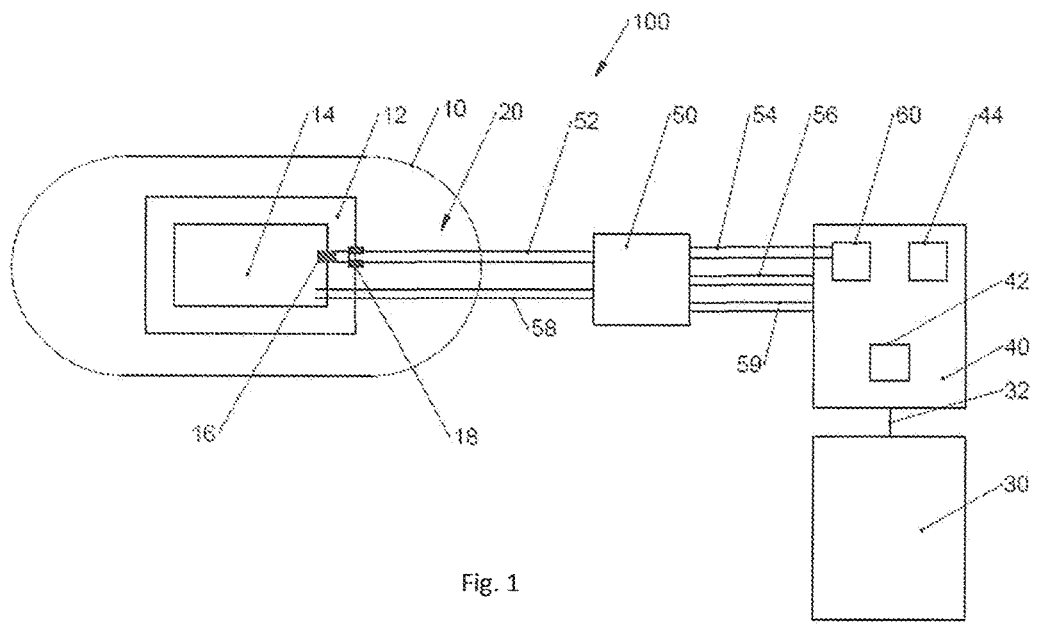
Fig. 1
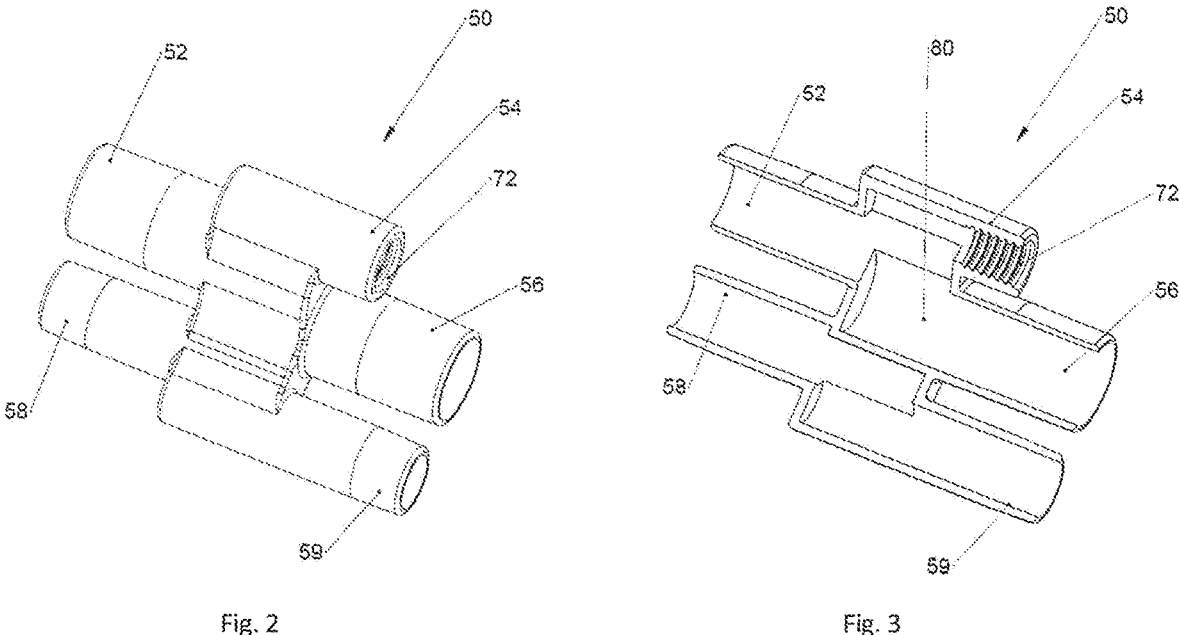
Fig. 2                                              Fig. 3

RECEPTACLE CONTAINER HAVING MONITORING UNIT

CROSS-REFERENCE TO RELATED APPLICATIONS

This application claims the benefit of priority under 35 U.S.C. 119 to German Patent Application No. 102022003990.7, filed Oct. 25, 2022; the disclosure of which is incorporated herein by reference in its entirely.

FIELD

The invention relates to a receptacle container for supplying a fluid into a body or body component having a connected monitoring unit in order to monitor a fluid reaction.

BACKGROUND

The receptacle container described here comprises a base body and an inner body which can be introduced detachably into the base body. The inner body comprises at least one valve device, which is arranged in the inner body such that in the event of gas generation of the or in the body (bodies), the valve device opens in order to release an escaping gas from the inner body of the receptacle container into the base body of the receptacle container, wherein the escaping gas escapes from the base body by means of a gas outlet opening thereof. The gas supply and discharge is ensured in the receptacle container by means of connected flexible tubular formations. Moreover, at least one gas source and a mixing system for metering is provided outside the base body, which generally comprises a flow rate controller and a positive or negative pressure device, in order to thus make fluid metering to and from the body individually settable.

The term body is understood hereinafter as a geometric body, a container, a vessel, a chamber, a space, or the human or animal body.

A receptacle container is known in the prior art under DE7439876, which discloses the flow and return of heating systems through a partition wall extending in the longitudinal direction by forming two parallel chambers. Furthermore, a double tube is disclosed which comprises a hose-like connecting piece having two separate pipe connections on the end face.

A device for storing pressurized gas, such as hydrogen and natural gas, is known from DE102020201172, wherein a storage line comprises at least one connecting piece for the gastight connection of at least one pressurized gas container. Furthermore, a safety element having a filter function and a shutoff function is disclosed.

A medical, in particular dental mask is disclosed in DE102015010684, which is connected by parallel tubes to a gas mixing system, which is disclosed, for example, in U.S. Pat. No. 10,882,016.

The object of the invention is to refine the prior art outlined above and to enable monitoring of a fluid reaction by way of a receptacle container, without the available space having to be restricted by additional tubes. A further object of the invention is to offer a module which avoids a direct additional intervention, for example, by an opening to be introduced into the receptacle chamber for taking samples.

Therefore, an apparatus for value determination comprising at least one proximally located fluid inlet and two distally located fluid outlets directly connected to the fluid inlet, which are led parallel to one another, is provided according to the invention.

In this case, in the transition between fluid inlet and the distally located fluid outlets, they are spatially opened, so that the fluid flow of the fluid inlet divides into two fluid outlets guided in parallel. It has proven to be particularly advantageous here for at least one fluid outlet to have a smaller diameter than the fluid inlet. A ratio of fluid inlet in the range of 2 to 5 to the fluid outlet of 0.5 to 1.5 is particularly advantageous in this case, wherein, for example, a ratio of the cross-sections to one another of fluid inlet to fluid outlet of 1.4:1; 2:1, 5.3:1, or 5:1 is particularly preferably used. The term fluid is understood as a gas, a liquid, a gas mixture, a liquid mixture, or a gas-liquid mixture.

In a further embodiment, a reversible, flexible measuring probe is provided in the at least one fluid outlet. In one particularly advantageous embodiment, this can extend through the given line of the fluid inlet up to the surface or into the body. The measuring probe is preferably designed to record measured values and is connected to a device for analyzing the measurement data with the aid of suitable tubular formations. In addition, a positive or negative pressure device can be provided, for example, to aspirate the escaping gas of the body by way of a slight negative pressure. The pressure device is understood as a compressor or also as a vacuum unit or negative pressure unit. Furthermore, the fluid outlet guided in parallel for receiving a measuring unit is designed such that it can be sealed using a closure if it is not to be used in the corresponding product embodiment.

Alternatively, the sample taking can also be carried out without a measuring probe through the line guided in parallel, wherein the inventors have recognized that a higher negative pressure has to be generated for this purpose in order to be able to perform a measured value determination that can be evaluated with sufficient accuracy.

In addition to the apparatus for measured value determination, a system is also claimed, wherein the system has a receptacle container, which can be applied to or integrated in the body, comprising a base body, and also an inner body detachably connectable therein. The base body is used in this case for the predominant purpose of discharging the excess fluid. Furthermore, the system consists of a flexible system made up of tubular formations, such as hoses, cable cores having at least one integrated hose, etc. At least two connectors are located thereon, which connect the receptacle container to a hose system on one side and a positive or negative pressure device and/or mixing system for providing or receiving fluids. Moreover, an apparatus having a proximally located fluid inlet and two distally located fluid outlets directly connected to the fluid inlet, which are guided parallel to one another, is provided in the flexible system made of tubular formations.

In a further particular embodiment, the apparatus for measured value determination is designed as an additional module optionally usable at different locations. The apparatus can preferably be incorporated in this case between two tubular formations as an adapter or in a further embodiment on the receptacle container, the pressure device, or the mixing system.

In this way, not only is the flexibility of usage increased, but rather cumbersome drilling into the receptacle container in order to integrate a measuring probe is avoided in particular during later retrofitting. In this way, escaping gases are reliably avoided, which can result in the performance drop of the overall system.

Furthermore, the apparatus for measured value determination designed as the module can be embodied from recyclable or compostable material in order to ensure disposal at the end of the product lifecycle or to ensure it is exchangeable in the event of contaminated material.

A further possible embodiment of the receptacle container according to the invention for supplying a fluid maps an engine compartment having injection channel in the automotive sector, wherein a space-saving measurement of the mixing ratio can be effectuated by the invention.

In a further embodiment of the receptacle container according to the invention for supplying a fluid, an OBD (onboard diagnostic) interface is formed for studying exhaust gas in a vehicle.

BRIEF DESCRIPTION OF THE DRAWINGS

In the following description of the figures, the present invention is described in more detail by way of example, wherein the explanation of the invention is to be made on the above-mentioned medical mask without any restriction of the technological field. Therefore, in the figures.

FIG. 1 shows a schematic view of the overall system in the incorporation of the apparatus for the purpose of a medical mask.

FIG. 2 shows a schematic view of the apparatus according to the invention.

FIG. 3 shows a schematic sectional view of the apparatus according to the invention.

DETAILED DESCRIPTION

Figure 4:
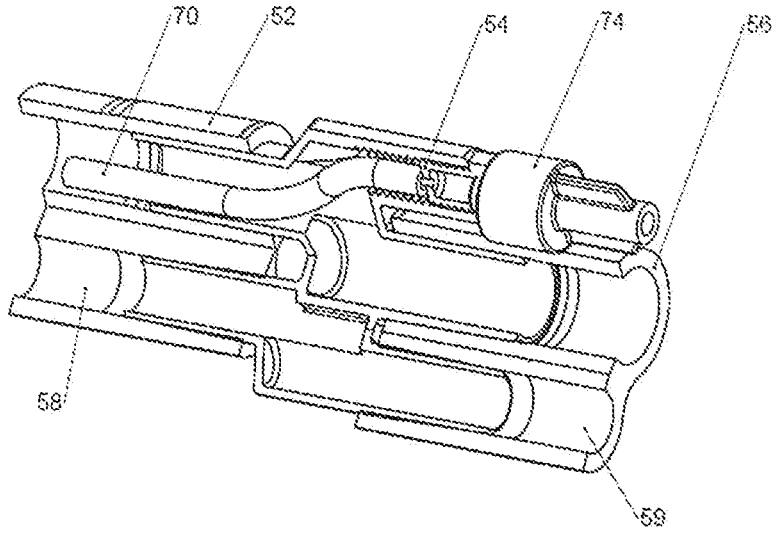
FIG. 4 shows a schematic view of the apparatus according to the invention having reversible flexible measuring probe.

Medical masks are often, but not exclusively, used during inhalations or respirations in medical and dental interventions for administering gases to a patient such as anesthetics, nitrous oxide, or oxygen. During the administration of these gases, it is advantageous for the patient if the operator, such as a physician or nurse, monitors the carbon dioxide concentration in the exhaled breath of the patient by means of end-tidal $CO_2$ measurement ($etCO_2$ value).

In this way, a dosing error, the depth of anesthesia or sedation, the respiratory behavior of the patient, such as breathing through the mouth when a nose mask is used, and also incorrect positioning of a mask can be diagnosed. For example, a dosing error would result in flatter respiration of the patient, due to which less carbon dioxide is exhaled, which in turn can be detected and output by means of visual or acoustic warning signals at the mixing system or another directly or indirectly connected analysis device.

Additionally, thereto, a display screen output can also take place in which one or more waveforms are recognizable on the display, which show a respiratory cycle. In the event of deviation from the normal waveform, the operator or a connected mixing system can automatically readjust the supplied dose. It is typical for oversedation, for example, that the respiratory activity is reduced and carbon dioxide can no longer be exhaled. Real-time monitoring of the patient, in particular with regard to the breathing pattern and the breathing status, can be carried out by the solution according to the invention. Influence can be taken on the given circumstance by suitable regulation and control devices or direct intervention of an operator.

FIG. 1 shows the system 100 according to the invention with regard to a medical mask as a receptacle container 10 having the apparatus 50 according to the invention. The receptacle container 10 comprises in this case a base body 12, such as an outer mask, and an inner body 14 detachably connectable to the base body 12. The inner body 14 is an inner mask in the embodiment of a medical mask. The base body 12 is used for the predominant purpose of discharging excess fluids, such as the exhaled gas or $CO_2$ of the patient.

The inner body 14 comprises at least one valve device 16, which is arranged in the inner body 14 such that when the body of the patient generates CO 2 gas, the valve device 16 opens in order to release escaping $CO_2$ gas from the inner body 14 of the receptacle container into the base body 12 of the receptacle container 10, wherein the escaping fluid (not shown) escapes therefrom by means of a gas outlet opening 18 of the base body 12.

The gas supply and gas discharge is ensured in the receptacle container 10 by means of connected flexible tubular formations 20. Moreover, at least one gas source 30 and a mixing system 40 connected by means of at least one line 32 for dosing are provided outside the base body 12, which generally comprise a flow rate regulator 42 and a positive or negative pressure device 44, in order to thus make fluid dosing to and from the inner body 14 and/or base body 12 individually settable.

Moreover, an apparatus 50 having a proximally located fluid inlet 52 and a distally located first fluid outlet 54, which is directly connected to the fluid inlet 52, and a distally located second fluid outlet 56, which is directly connected to the fluid inlet 52, and which are guided parallel to one another, is provided in the flexible system made of tubular formations 20. A further continuous nitrous oxide line (not shown) is provided instead of the nitrous oxide line 58, 59 in the apparatus 50 for feeding through fluid, in particular the nitrous oxide mixture to the patient.

In a further embodiment of the apparatus 50, it has a proximally located nitrous oxide outlet 58 and a distally located nitrous oxide inlet 59 arranged offset thereto (cf. FIG. 2) for feeding through the fluid (not shown).

Furthermore, the mixing system 40 can also comprise a device for analysis 60. The device for analysis 60 is used to evaluate the measurement data of the apparatus 50 which are provided by means of a measuring probe 70 (cf. FIG. 4).

FIG. 2 shows an apparatus 50, described in more detail hereinafter, for measured value determination, for example of an $etCO_2$ value, having at least one fluid inlet 52 located proximally to the receptacle container 10 (cf. FIG. 1) and two distally located fluid outlets 54, 56 connected directly to the fluid inlet 52, which are guided parallel to one another. In one particular embodiment, a connecting element, such as the thread 72 shown, is provided as a possible embodiment in the fluid inlet 52 and/or in the fluid outlets 54, 56. Further connecting elements could be, for example, plug-in or press-in systems or screw connections, welds, or again detachable systems such as bayonet fittings.

The thread 72 in the distally located first fluid outlet 54 is provided for the detachable connection of the measuring probe 70 or a closure 74 if a measuring probe 70 is not desired in the treatment and the access is to be closed.

In an alternative embodiment, the measuring probe 70 can also be led up to the inner body 14 (cf. FIG. 1), in particular in the example of the medical mask up to the inner mask or up to the nose of the patient. In this way, it is unimportant whether the line of the fluid inlet 52 is gas guiding or gas discharging.

In FIG. 3, in the transition 80 between proximally arranged fluid inlet 52 and distally located fluid outlets 54, 56, they are spatially opened, so that the fluid flow (not shown) of the fluid inlet 52 is divided into two fluid outlets

54, 56 guided in parallel. It has proven to be particularly advantageous here that the first distally guided fluid outlet 54 has a smaller diameter than the second distally guided fluid outlet 56. Particularly preferably, a ratio of fluid inlet in the range of 2 to 5 to the fluid outlet of 0.5 to 1.5 is particularly advantageous, wherein, for example, a ratio of the cross-sections to one another of fluid inlet to fluid outlet of 1.4:1; 2:1, 5.3:1, or 5:1, in particular 176:127 or 110:21 is particularly preferably used.

FIG. 4 shows a reversible flexible measuring probe 70 in the at least one distally located fluid outlet 54 as already mentioned above. Plastic hoses or flexible plastic tubes are suitable here as the measuring probe 70, for example. However, depending on the area of application, other measuring probes, such as intelligent or "smart" systems, for example, having sensor cleaning function, direct data transfer, or the like are also proposed. In one particular embodiment, the flexible measuring probe 70 can extend into the inner body 14 (cf. FIG. 1).

The measuring probe 70 is preferably designed for etCO$_2$ value recording and is connected to a device for analyzing 60 the measurement data with the aid of suitable hoses 20. In addition, a slight negative pressure can be provided by the pressure device 44 in order to aspirate the escaping gas of the body or the patient (not shown). Furthermore, the fluid outlet 54 distally guided in parallel to the second fluid outlet 56 is designed to receive a measuring unit 70 such that it can be sealed off using a closure 74. The Luer lock which is widespread in medical technology has proven to be advantageous for this purpose.

Alternatively, the sample taking can also be carried out without measuring probe 70 through the tubular formation 20 guided in parallel, wherein the inventors have recognized that a higher negative pressure has to be generated for this purpose and a larger dimensioned pressure device 44 has to be provided for this purpose, in order to be able to perform an etCO$_2$ value determination that can be evaluated. However, depending on the constitution of the patient, an elevated pressure can be perceived as unpleasant.

The invention claimed is:

1. An apparatus comprising:
   a proximally located first fluid inlet;
   two distally located first fluid outlets, the first fluid outlets directly connected to the first fluid inlet, wherein the first fluid inlet and the first fluid outlets are guided in parallel to one another,
   a proximally located second fluid outlet;
   a distally located second fluid inlet, the second fluid outlet directly connected to the second fluid inlet, wherein the second fluid inlet and the second fluid outlet are guided in parallel to one another, and wherein the second fluid outlet is fluidically separate from the first fluid outlets, and the first fluid inlet is fluidically separate from the second fluid inlet; and
   a reversible flexible measuring probe, wherein at least one first fluid outlet is configured to receive the reversible flexible measuring probe.

2. The apparatus of claim 1, wherein, in a transition between the first fluid inlet and the first fluid outlets, these are spatially opened, so that fluid flow from the first fluid inlet is divided into two first fluid outlets guided in parallel.

3. The apparatus of claim 1, wherein at least one of the first fluid outlets has a smaller diameter than the first fluid inlet.

4. The apparatus of claim 1, wherein the flexible measuring probe is configured to extend through the first fluid inlet up to or into an inner body of the apparatus.

5. The apparatus of claim 1, wherein at least one first fluid outlet is capable of being sealed off by a closure.

6. The apparatus of claim 1, wherein at least one first fluid outlet is connected to a positive or negative pressure device.

7. The apparatus of claim 1, wherein the flexible measuring probe is configured to measure a CO$_2$ value.

8. The apparatus of claim 1, wherein the second fluid inlet is configured to receive a gas comprising nitrous oxide.

9. The apparatus of claim 1, wherein the second fluid inlet is guided in parallel to both the two first fluid outlets.

10. The apparatus of claim 1, wherein a ratio of a diameter of the first fluid inlet to the diameter of each of the two first fluid outlets is selected from the group consisting of:
    between 2:0.5 and 2:1.5; and
    between 5:0.5 and 5:1.5.

11. The apparatus of claim 1, wherein a ratio of cross-sections of the first fluid inlet to the two first fluid outlets is selected from the group consisting of 1.4:1; 2:1, 5.3:1, 5:1, 176:127, and 110:21.

12. The apparatus of claim 1,
    wherein the two first fluid outlets each comprise a first fluid outlet axis,
    wherein the first fluid inlet comprises a first fluid inlet axis,
    wherein the second fluid inlet comprises a second fluid inlet axis, and
    wherein the second fluid outlet comprises a second fluid outlet axis.

13. The apparatus of claim 12,
    wherein each of the first fluid outlet axes are offset from each of:
    the first fluid inlet axis;
    the second fluid inlet axis; and
    the second fluid outlet axis.

14. A system comprising:
    a receptacle container that can be applied or connected to a body, the receptacle container comprising a base body, and an inner body detachably connectable therein, and wherein the receptacle container is connected by flexible tubular formations to a system for providing fluids, furthermore comprising an apparatus comprising:
    a proximally located first fluid inlet;
    two distally located first fluid outlets, the first fluid outlets directly connected to the first fluid inlet, wherein the first fluid inlet and the first fluid outlets are guided in parallel to one another,
    a proximally located second fluid outlet; and
    a distally located second fluid inlet, the second fluid outlet directly connected to the second fluid inlet, wherein the second fluid inlet and the second fluid outlet are guided in parallel to one another, and wherein the second fluid outlet is fluidically separate from the first fluid outlets, and the first fluid inlet is fluidically separate from the second fluid inlet.

15. The system of claim 14, wherein the flexible tubular formation is also connected to a pressure device and/or mixing system, in addition to the system for providing fluids.

16. The system of claim 14, wherein the second inlet is guided in parallel to both the first fluid inlet and the two first fluid outlets.

17. The system of claim 14,
    wherein the two first fluid outlets each comprise a first fluid outlet axis,
    wherein the first fluid inlet comprises a first fluid inlet axis,

wherein the second fluid inlet comprises a second fluid inlet axis, and wherein the second fluid outlet comprises a second fluid outlet axis.

18. The system of claim 17, wherein each of the first fluid outlet axes are offset from each of:

the first fluid inlet axis;

the second fluid inlet axis; and the second fluid outlet axis.

* * * * *